(12) United States Patent
Bouchard et al.

(10) Patent No.: US 10,502,624 B2
(45) Date of Patent: Dec. 10, 2019

(54) COMPACT APPARATUS FOR LASER INDUCED BREAKDOWN SPECTROSCOPY AND METHOD THEREFOR

(71) Applicant: National Research Council Canada, Ottawa (CA)

(72) Inventors: Paul Bouchard, Montreal (CA); Mohamad Sabsabi, Longueuil (CA); Francois Doucet, Laval (CA); Lütfü Celebi Özcan, Montreal (CA)

(73) Assignee: National Research Council Canada, Ottawa (CA)

( * ) Notice: Subject to any disclaimer, the term of this patent is extended or adjusted under 35 U.S.C. 154(b) by 211 days.

(21) Appl. No.: 15/524,585

(22) PCT Filed: Nov. 6, 2015

(86) PCT No.: PCT/CA2015/051155
§ 371 (c)(1),
(2) Date: May 4, 2017

(87) PCT Pub. No.: WO2016/070290
PCT Pub. Date: May 12, 2016

(65) Prior Publication Data
US 2018/0283947 A1    Oct. 4, 2018

Related U.S. Application Data

(60) Provisional application No. 62/076,798, filed on Nov. 7, 2014.

(51) Int. Cl.
*G01J 3/443*    (2006.01)
*G01N 21/71*    (2006.01)
*G01J 3/02*    (2006.01)

(52) U.S. Cl.
CPC ............. *G01J 3/443* (2013.01); *G01J 3/0208* (2013.01); *G01J 3/0243* (2013.01);
(Continued)

(58) Field of Classification Search
CPC ........ G01J 3/443; G01J 3/0208; G01J 3/0243; G01N 21/718; G01N 2201/0221; G01N 2201/0636; G01N 2201/0638
See application file for complete search history.

(56) References Cited

U.S. PATENT DOCUMENTS 8,076,624 B1 * 12/2011 Barchers .............. F41H 13/005
                                                    250/201.9
2010/0197116 A1 * 8/2010 Shah .................... B23K 26/38
                                                    438/463

(Continued)

OTHER PUBLICATIONS

International Searching Authority, PCT/CA2015/051155, "The International Search Report and the Written Opinion of the International Searching Authority", 7 pages, dated Dec. 4, 2015.

*Primary Examiner* — Dominic J Bologna
(74) *Attorney, Agent, or Firm* — McKee, Voorhees & Sease, PLC

(57) ABSTRACT

The present invention provides a method and compact apparatus for laser induced breakdown atomic emission spectroscopy from a targeted sample having a laser generating a laser beam, the laser beam directed to the sample, optical means for manipulating the laser beam in order maximize laser fluency at the target surface of the sample, the laser beam generating ablation and plasma emission from the sample at the target surface, an emission spectrometer having a detector for detecting a plasma plume from the plasma emission.

23 Claims, 11 Drawing Sheets

(52) U.S. Cl.
CPC ... *G01N 21/718* (2013.01); *G01N 2201/0221* (2013.01); *G01N 2201/0636* (2013.01); *G01N 2201/0638* (2013.01)

(56) References Cited

U.S. PATENT DOCUMENTS

| | | | |
|---|---|---|---|
| 2012/0314214 A1* | 12/2012 | Alexander | G01J 3/443 356/318 |
| 2013/0062323 A1* | 3/2013 | Hassan | G01N 21/718 219/121.62 |
| 2014/0204375 A1 | 7/2014 | Day | |
| 2014/0204376 A1 | 7/2014 | Day | |
| 2014/0204377 A1 | 7/2014 | Day | |
| 2014/0204378 A1 | 7/2014 | Day | |
| 2015/0132789 A1* | 5/2015 | Bornheimer | G01J 3/42 435/29 |

* cited by examiner

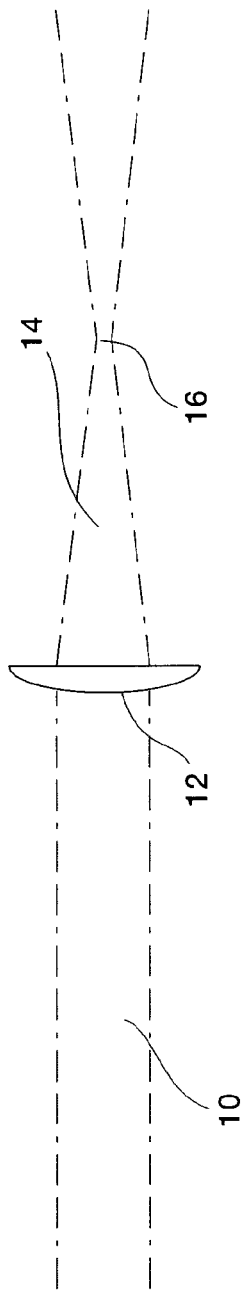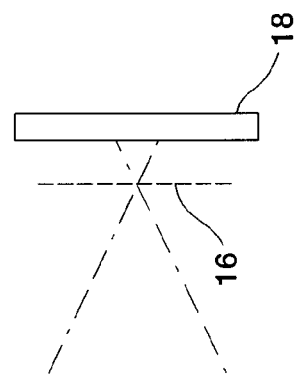

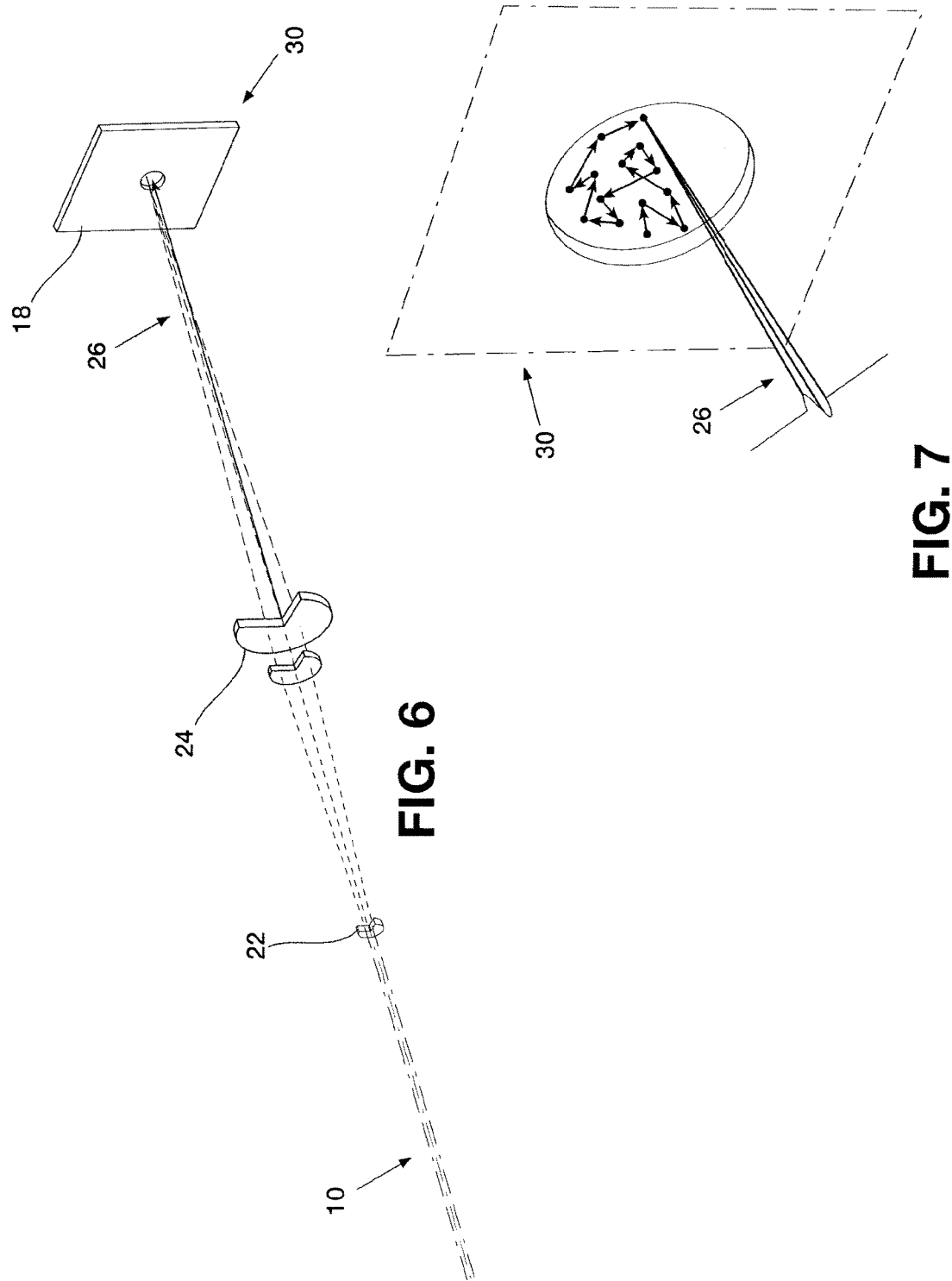

COMPACT APPARATUS FOR LASER INDUCED BREAKDOWN SPECTROSCOPY AND METHOD THEREFOR

FIELD

The present invention relates to analytical instrumentation and methods for analyzing the chemical content of a sample. More specifically, the present invention relates to a method and apparatus for performing laser induced breakdown atomic emission spectroscopy on a targeted sample.

BACKGROUND

Laser induced breakdown spectroscopy (commonly known as "LIBS") is a known process for detecting the chemical composition of a sample. LIBS involves focussing a laser on a target sample in order to generate sufficient heat to create ablation (i.e. material removal by vaporization of said material) of the target sample. As the sample material is initially ablated, plasma is created and emitted from the target sample at extremely high temperatures. The emitted plasma contains excited, disassociated atoms that emit light of a particular frequency when heated to a specific excitation temperature that can be detected and analyzed by a spectrometer in order to determine the chemical composition of the ablated sample.

More specifically, as the plasma cools, electrons from the various elements that comprise the sample fall from various excited states to lower energy states, emitting photons in the process. The frequency of these emitted photons is proportional to the energy of the photons and is, in turn, equal to the difference between the two energy states. The frequency (or its inverse, wavelength) and intensity of the photons can then be measured by a spectrometer-type detector to determine chemical composition of the sample spot where the plasma was created.

LIBS is typically minimally destructive, non-invasive and requires minimal sample preparation. It can be completed very rapidly and from a remote location, which makes it an excellent choice for applications where high volumes of analyses are required. LIBS can be used on any type of target sample and can detect any element on the periodic table.

However, known methods and apparatuses for conducting LIBS have a host of challenges and disadvantages. For example, many LIBS systems require relatively high powered lasers in order to effectively ablate the target sample. Further, as the target surface deteriorates the proper conditions for ablation may vary and many known methods are not well suited to adjusting the laser source in real time to maintain ideal ablation conditions. Finally, many known LIBS apparatuses are rather large and non-suited to applications requiring portable and compact instruments.

As will be readily understood by the skilled person, plasma creation is dependent mainly on the power density of the laser spot rather than the total overall power of the laser source. Therefore, a lower power laser must be focused to a smaller spot size to attain sufficient power density for plasma ignition. Therefore, in order to generate a sufficient energy density for plasma ignition in the sample region being analyzed, currently available low power lasers are typically focused down to a much smaller spot size than what would be required when using more powerful bench top lasers (i.e.: on the order of 5 $\mu$m to 100 $\mu$m).

It is therefore possible to use a much lower powered laser, however the main drawback of using lower power lasers is that the ablation area on the sample will be reduced accordingly as the laser post size is reduced, resulting in a more localized measurement, less plasma ablation and, as a result, less photons emitted from the sample. Therefore, detection is less reliable in these prior art arrangements.

Further, a small sample area (5 $\mu$m to 100 $\mu$m in diameter) creates additional problems that must be addressed when using a lower energy laser in practical applications. First, the laser must ideally be focused at the location where the analysis is required, which for most applications, is the surface of the sample.

However and as will be appreciated by the skilled person, minor deviation in the laser's focus results in inefficient and incomplete ablation at the sample surface, leading to incomplete plasma formation. As a result, the generated plasma is not representative of the actual sample being tested which can lead to erroneous analytical results. Also, it must be appreciated that in many real-world cases the samples being tested are not completely smooth or flat, exacerbating these complications.

A second issue that can present itself is sample cleanliness. LIBS is a very sensitive technique and the depth of the region being analyzed is typically just several microns deep across a sample area diameter of 5 $\mu$m to 100 $\mu$m. It can therefore be quite important that the surface being analyzed is truly representative of the sample and is therefore free of dirt, oils, oxidation and any other type of contamination. In prior art solutions, it is typical to fire a number of "cleaning shots" with the laser prior to analyzing the spectral data to determine composition. These cleaning shots can burn off superfluous material from the sample surface, permitting the analysis of the underlying clean material. For these cleaning tests to be effective, the laser must be properly focused on the contaminated sample surface.

A third issue that can present itself when using low powered lasers is that the sample can be inhomogeneous. Therefore, in some arrangements it can be required to fire the laser at several different locations on the surface of the sample and average the results.

One way that low power lasers can be used to create and maintain laser ablation is by varying the optimal distance of the focusing lens relative to the sample surface (i.e: the focal length of the focusing lens) as will be readily appreciated by the skilled person. These adjustments to the focal length are typically on the order of a few micrometers.

Available prior art solutions teach the concept of incrementally adjusting the focal length using, for example, a stepwise motor as taught in US Patent Publication Nos. 2014/0204375, 2014/0204377, 2014/0204376 and 2014/0204378. In these documents, the position of a focusing lens is varied in a stepwise, incremental manner based on output received from a spectrometer oriented to analyze the plasma emission. This spectrometer output is employed in what is effectively a feedback loop in order to adjust the position of the focusing lens relative to the sample in an incremental manner until the spectrometer output indicates a maximum or near maximum intensity of plasma formation. In short, the focal length (and therefore, efficiency of plasma formation) is adjusted based on the efficiency of the spectrometer operation.

This prior art approach is limited as adjusting the focusing lens through incremental movements and based on output from the spectrometer does not permit sufficient resolution and makes the process somewhat impractical as it can permit only rough evaluation rather than finely tuned measurement. Accordingly, a skilled person would appreciate that these prior art solutions are best suited to applications where the sample has relatively smooth surfaces (i.e.: flat polished samples) and is not ideally suited for use in connection with rough surfaces (mining samples, soil, oxide, metallic alloys etc.).

Accordingly, there is a need for an improved method and apparatus for performing laser induced breakdown atomic emission spectroscopy on a targeted sample in a compact format and using low power lasers.

BRIEF SUMMARY

An objection of the present invention is to provide a method and compact apparatus for performing laser induced breakdown atomic emission spectroscopy on a targeted sample.

In accordance with an aspect of the present invention, there is provided a method of laser induced breakdown spectroscopy having the steps of directing a laser beam to a target plane on a sample, the target plane located on a proximal surface of the sample, manipulating the laser beam to substantially maximize threshold fluency at the target plane, and generating ablation and plasma emission from the sample at the target plane.

In accordance with an aspect of the present invention, there is provided an apparatus for laser induced breakdown spectroscopy of a sample having a laser generating a laser beam, the laser beam directed to the sample, optical means for manipulating the laser beam to substantially maximize threshold fluency at the target plane, the laser beam generating ablation and plasma emission from the sample at the target surface and an emission spectrometer having a detector for detecting a plasma plume from the plasma emission.

BRIEF DESCRIPTION OF THE DRAWINGS

The present invention will be better understood in connection with the following drawings, in which:

FIG. 2 is a diagram of at least one embodiment of the present invention illustrating optical means being employed to increase fluence at a focusing plane of a laser beam by reducing the diameter of the laser beam;

FIG. 3 is a diagram of at least one embodiment of the present invention illustrating the focusing plane of a reduced laser beam and the target surface;

FIG. 6 is a diagram illustrating one embodiment of the present invention wherein the target surface is sampled at a plurality of positions;

FIG. 7 is a close-up view of the target surface illustrated in FIG. 6;

DETAILED DESCRIPTION OF THE EMBODIMENTS

Figure 1:
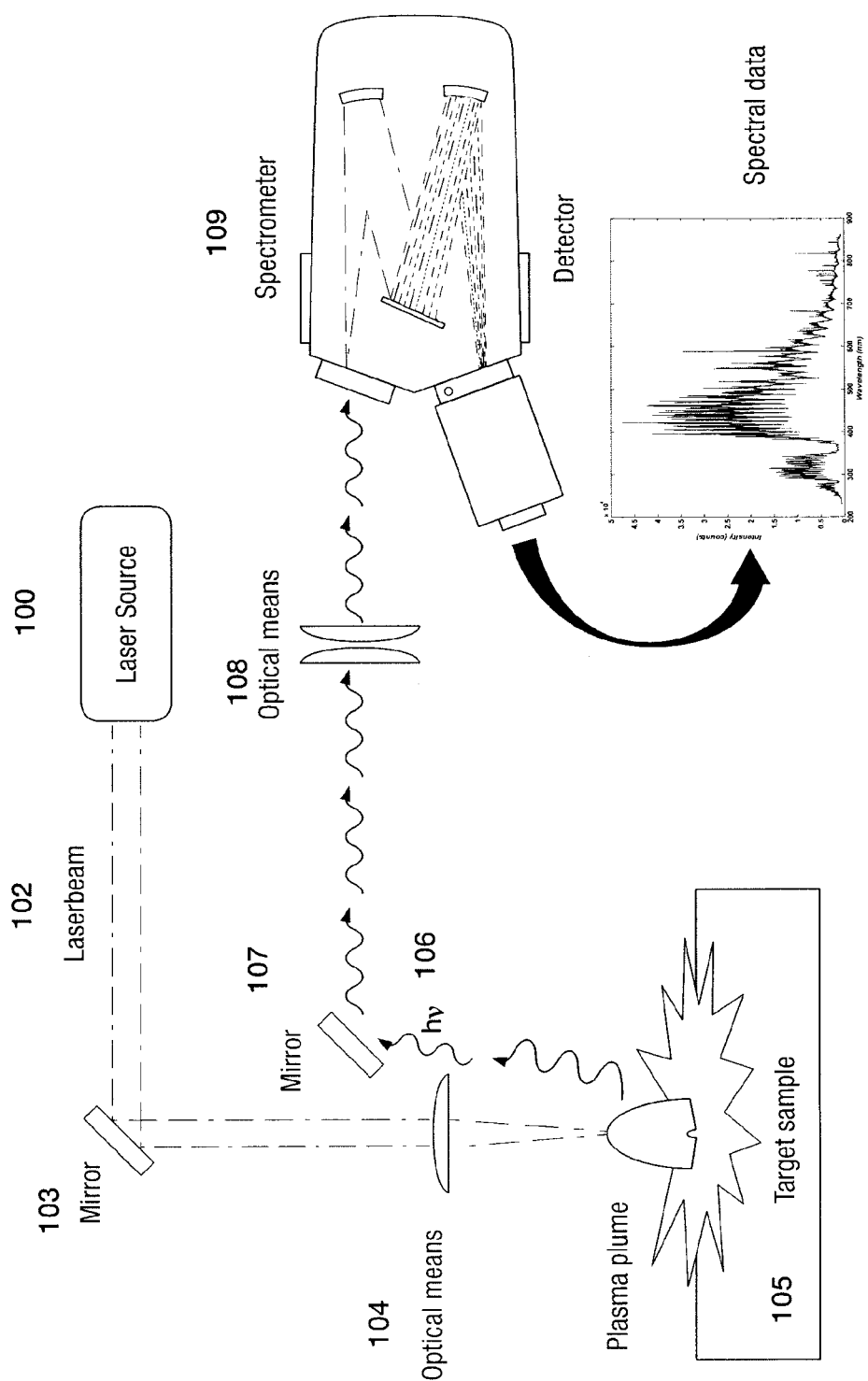
FIG. 1 is a diagram of a LIBS apparatus in accordance with embodiments of the present invention.

The present invention provides a method and apparatus for performing laser induced breakdown spectroscopy ("LIBS") using a compact apparatus that has been reduced with respect to weight and volume. Producing an apparatus having the requisite physical dimensions typically involves employing constituent components that often have lower performance levels in comparison to larger versions of these same components.

In at least one embodiment, the present invention can address a number of common challenges encountered when employing low energy laser pulses in LIBS applications.

First, in at least one embodiment of the present invention the laser spot is optimized on the sample surface through optimization of the focus of the focusing lens by employing an electrically tunable focusing lens rather than physically moving the position of the focusing lens relative to the sample surface. This can lead to a number of advantages given that the focusing lens itself does not have to move. For example, this arrangement can permit a fast scan in order to determine the optimal tuning of the focusing lens.

In at least one embodiment, it is contemplated that a first level of optimization can be achieved by integrating the light using a sensitive photodiode detector, as will be discussed in further detail below.

Then, optionally, in a second step of fine tuning, the optimal tuning of the focusing lens can be achieved by employing the ratio of ionic lines to atomic lines for the same element present in the plasma. This fine tuning can be carried out by collecting the light through a spectrometer and using the ratio of ionic lines to atomic lines for the same element, as will be described in further detail below.

As will be readily appreciated by the skilled person, the ratio of ionic lines to atomic lines for a particular element is sensitive to variations of the fluency of laser spot at the sample surface, which in turn delivers a higher resolution.

Further to this point, when the focal length of the focusing lens approaches the optimal focusing distance the laser fluence at the sample surface gradually increases, as will be appreciated by the skilled person. As the ablation threshold of the sample material is reached, a plasma plume is formed which radiates light in the form of spectral lines associated with the constituent elements of the sample present in the plasma.

For the purpose of identifying the optimal location of the laser beam spot on the target plane, one can monitor the intensity of an atomic spectral line $I_a$. It is known from atomic physics that the intensity of an atomic spectral line is a function of the population density of the upper level $N_a$ and the excitation temperature $T_{exc}$, through the following Boltzmann relation:

$$I_a = \frac{hc}{4\pi} \frac{g_a A_a}{\lambda_a} \frac{N_a}{U(T_{exc})} \exp\left(-\frac{E_{exs,a}}{kT_{exc}}\right)$$

Where h is the Planck constant, c is the velocity of light, $g_a$ is the statistical weight and $A_a$ the Einstein coefficient of the excited level of the atomic transition, $\lambda_a$ is the emission wavelength of the atomic transition, $N_a$ is the number density of atoms in the upper level, $T_{exc}$ is the excitation temperature, $U(T_{exc})$ is the partition energy, k is the Boltzmann constant and $E_{exc,a}$ the atomic excited level energy.

It is also known that the values of $N_a$ and $T_{exc}$ will vary with the laser fluence in the target plane (the other parameters of the above equation being constant with respect to the fluence), such that the intensity $I_a$ will be maximum when the fluence also reaches its maximum value. One can also consider monitoring the ratio of the intensity of ionic species line over an atomic species line $I_i/I_a$ for the same purpose. The expression for this ratio is given by the Saha relation:

$$\frac{I_i}{I_a} = \frac{2(2\pi m_e k)^{3/2}}{h^3} \frac{1}{N_e} \left(\frac{g_i A_i \lambda_a}{g_a A_a \lambda_i}\right) T_v^{3/2} \exp\left(-\frac{E_{ion}}{k\,T_e}\right) \exp\left[\frac{-(E_{exc,i} - E_{exc,a})}{k\,T_{exc}}\right]$$

where $m_e$ is the mass of the electron, $N_e$ is the electron number density, $g_i$ is the statistical weight and $A_i$ the Einstein coefficient of the excited level of the ionic transition, $\lambda_i$ is the emission wavelength of the ionic transition, $T_e$ is the ionization temperature, $E_{ion}$ is the ionization energy and $E_{exc,i}$ the ionic excited level energy Unlike the atomic line intensity, the $I_i/I_a$ ratio is also a function of the ionization temperature $T_e$ and of the electron number density $N_e$. Now, it is known to the skilled person that in the case of a LIBS plasma, this ratio is more sensitive to the variation of the laser fluence than the atomic line intensity. Therefore, using the $I_i/I_a$ ratio as a probing parameter for the determination of the optimal focusing distance will allow achieving a significantly more accurate measurement of the optimal distance sought. In particular, this feature is an important parameter for the effective positioning of the laser beam in the case of targets with rough or uneven surfaces, where it will allow a more effective and robust optimization of the performance of the present apparatus.

The ionic line intensity $I_i$ alone can also be used to enhance the focusing precision of the tunable lens, as a complementary method to the one based on the signal provided by the integrating photodiode detector. This alternate approach stems from the outstanding sensitivity of the ionic lines to the laser fluence variations, as can be deduced from the above expressions. Being spatially and spectrally integrated, the light field detected by the photodiode does not show the same dependency on the fluence as the ionic line, and as such behaves more like the intensity coming from an atomic line. As a consequence, the profile of variation of the ionic line intensity versus the tuning parameter (focal length) of the focusing lens is narrower than the photodiode signal profile, as illustrated by the experimental data of FIG. 12. As a result, this feature can provide a better tuning sensitivity, better spatial resolution and robustness than the method based on the spatial and spectral integration of light field emitted from the plasma plume alone.

The present invention can also be well suited to applications where the sample surface has varying degrees of cleanliness and homogeneity. As several points can be sampled by controlling the depth of field, this can result in an efficient sample surface cleaning without harming the accuracy of the measurement through the "tunneling" effect that can occur when successive laser shots are taken at the same location on the sample surface.

In at least one embodiment, the present invention can also provide improved ways of collecting light emitted from the plasma using achromatic reflective optics such as robust, parallel concave mirrors. These configurations are unaffected by the distance between mirrors and can have a bigger aperture than available prior art solutions, which allows integrating more light, thereby increasing sensitivity and compensating for the otherwise low number of photons received by the spectrometer.

With reference to FIG. 1, at least one embodiment of the present LIBS apparatus is illustrated and can include a laser source 100 that produces a laser beam 102 that is directed, often by way of mirrors 103, through optical means 104 to a target sample 105. Once the laser beam 102 reaches the target sample 105, ablation occurs at the target surface and light 106 is emitted (i.e: $h_v$), redirected by mirrors 107, manipulated by further optical means 108 and detected by a spectrometer 109 having a detector for detecting and analyzing spectral data.

In particular, the main components affected when trying to produce a compact apparatus are the laser source and the spectrometer. Specifically, component laser sources tend to produce laser beams that have significantly lower beam energies than larger counterparts.

LIBS performance is largely related to the laser sensitivity. Laser sensitivity is in turn related, in part, to the laser fluence on the target surface. Laser fluence is a measurement of laser energy per unit surface and is measured in Joules per $cm^2$. A threshold laser fluence level must be reached to actually achieve ablation of the sample material at the target surface and to generate a plasma plume with the proper radiance for efficient spectrometry.

The appropriate threshold laser fluence for LIBS is difficult to achieve with a low energy laser beam. However, laser fluence can be increased by decreasing the surface area of the laser beam (or in other words, the diameter of the circular laser beam) as seen in this equation:

$$\mathcal{F} = \frac{E}{A} \text{ where } \mathcal{F} = \text{fluence,}$$

$E$ = laser energy and $A$ = area of laser beam

With reference to FIG. 2, one way that the area/diameter of an incident laser beam 10 can be reduced is by using a converging optical component (such as, by way of non-limiting example, a planoconvex lens) 12 with a relatively short focal length to reduce the diameter of the laser beam in order to create a resultant reduced diameter laser beam 14 having a smaller surface area/smaller diameter at its focussing plane 16, as seen in FIG. 2.

However and as seen in FIG. 3, one of the challenges of this approach is that positioning of the focussing plane 16 of the laser beam such that it is substantially coincident with a target surface 18 of a sample is difficult, as the fluence of the laser beam varies greatly over a very small zone on either side of the focusing plane 16. Therefore, it becomes important to precisely manipulate the focussing plane 16 in order to substantially maximize laser fluency at the target surface 18.

Figure 4:
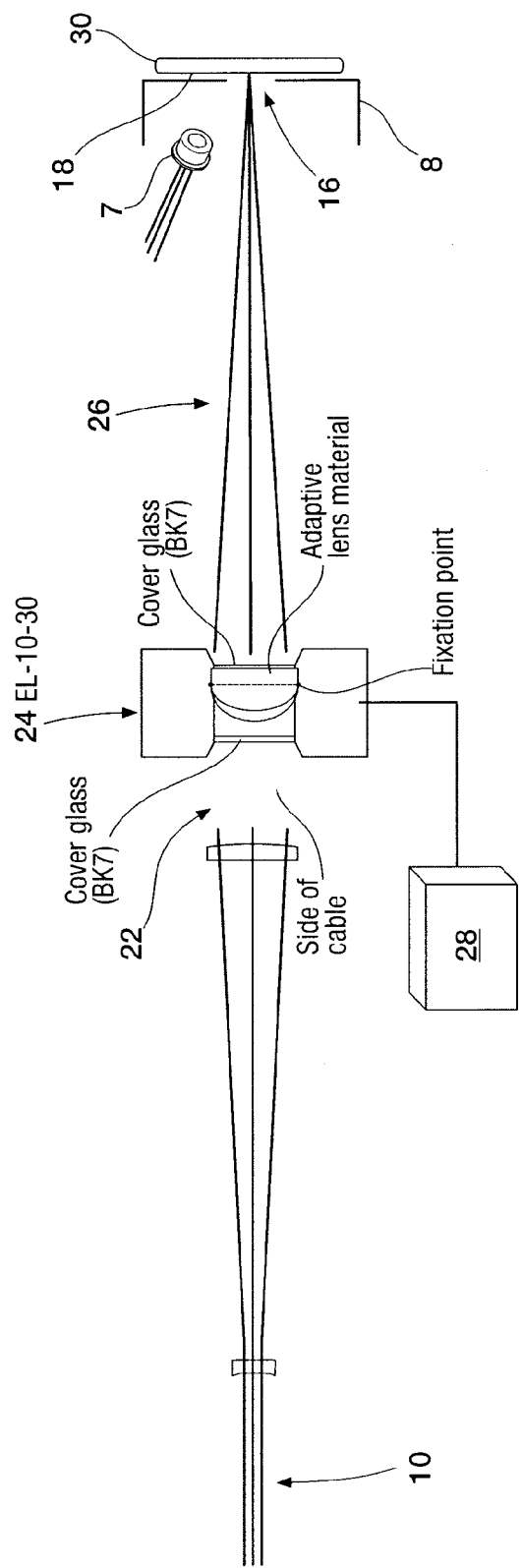
FIG. 4 is a diagram of at least one embodiment of the present invention wherein a laser beam is manipulated such that a focusing plane of the laser beam is substantially coincident with the target surface.

The present invention provides a method and apparatus for addressing this challenge. As seen in FIG. 4, one embodiment of the present invention is illustrated where an incident laser beam 10 is expanded using optional pre-optical lenses 22 and directed to optical means 24 which reduce the diameter and focal length of the laser beam to create a reduced diameter resultant laser beam 26 such that the focussing plane 16 of the laser beam is substantially coincident with the target surface 18 of a sample 30 in order to substantially maximize laser fluency at the target surface 18. This permits ablation of the sample material and as a result plasma is emitted from the target surface. This plasma emission can be detected by a detector 28 which is optically coupled to a spectrometer (not shown). The spectrometer can in turn provide spectral analysis of the light emitted in connection with the plasma emission and accordingly, the chemical composition of the sample.

It will be readily understood that any laser source is contemplated for use in connection the present invention. Similarly, any suitable spectrometer and detector therefor are contemplated for use in connection with the present invention, as will be readily understood by the skilled person.

It is contemplated that optical means 24 can take a wide variety of forms as will be readily understood by the skilled person, including, but not limited to, single-axis electronically tunable lenses, triple-axis electronically tunable lenses, focusing lenses and beam reducing lenses, among other suitable arrangements and combinations thereof for reducing laser beam diameter and shortening laser beam focal length.

Electronically tunable lenses are well suited to many of the embodiments described herein as they typically can have a small form factor, are lightweight, have fast response times and no or minimal mechanical moving parts that require maintenance and can be prone to failure.

Figure 5:
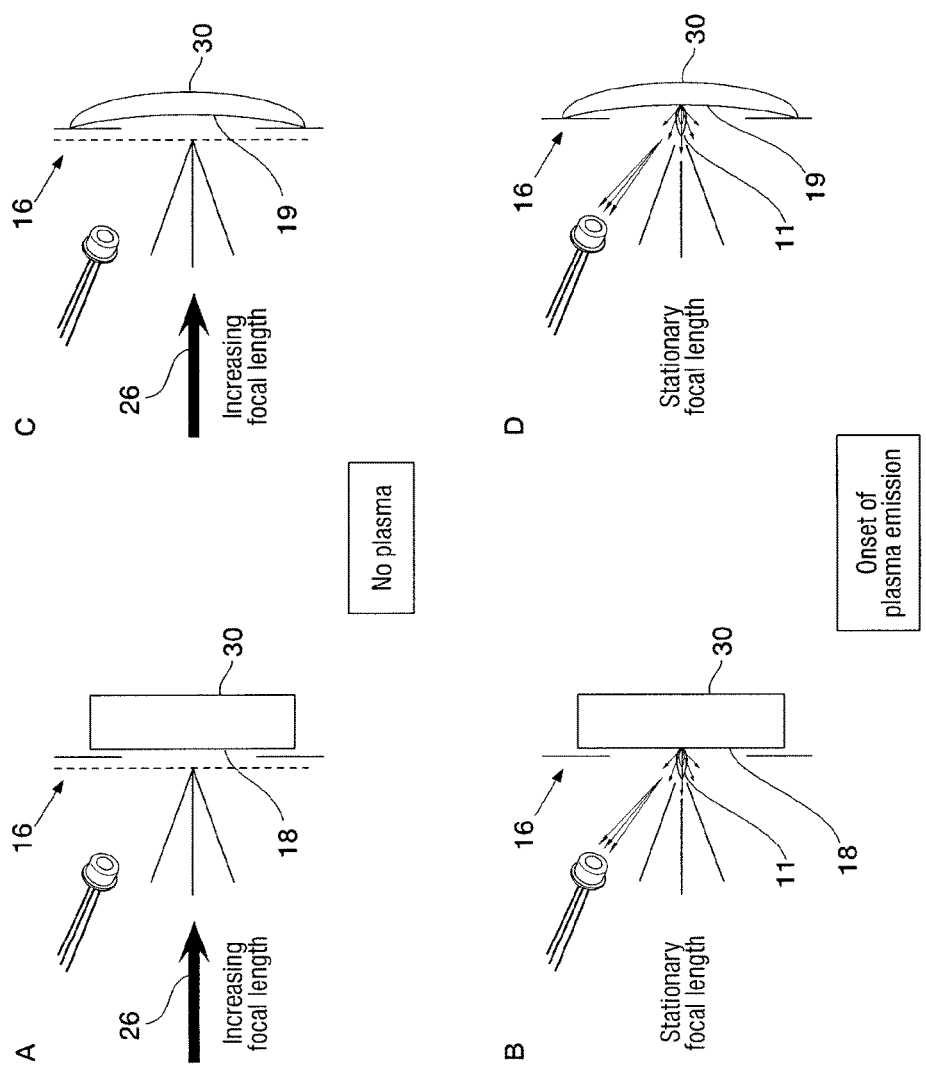
FIGS. 5A through 5D are diagrams illustrating a number of ways in which a laser beam can be manipulated in a manner to maximize ablation at the target surface in accordance with FIG. 4.

FIG. 5A through 5D illustrate how at least one embodiment of the present invention can be employed to substantially maximize laser fluency at a target surface. Initially, as seen in FIG. 5A, focusing plane 16 of resultant laser beam 26 is not coincident with target plane 18 of the sample 30. Accordingly, the focal length of incident laser beam must be increased such that the focusing plane 16 of the resultant laser beam 26 is coincident with the target plane 18 in order to generate ablation and plasma emission at the target surface 18, as seen in FIG. 5B.

Laser fluency can be substantially maximized at the target sample in a number of ways: the focusing lens can be electrically tuned in a number of ways that will be readily apparent to the skilled person, including: rough adjustment can be achieved through collecting the whole light with a photodiode, fine tuning can be achieved using a ratio of ionic lines to atomic lines of the same target matrix element, or by monitoring the intensity of a single ionic line of the element, as discussed in further detail above.

Figure 11:
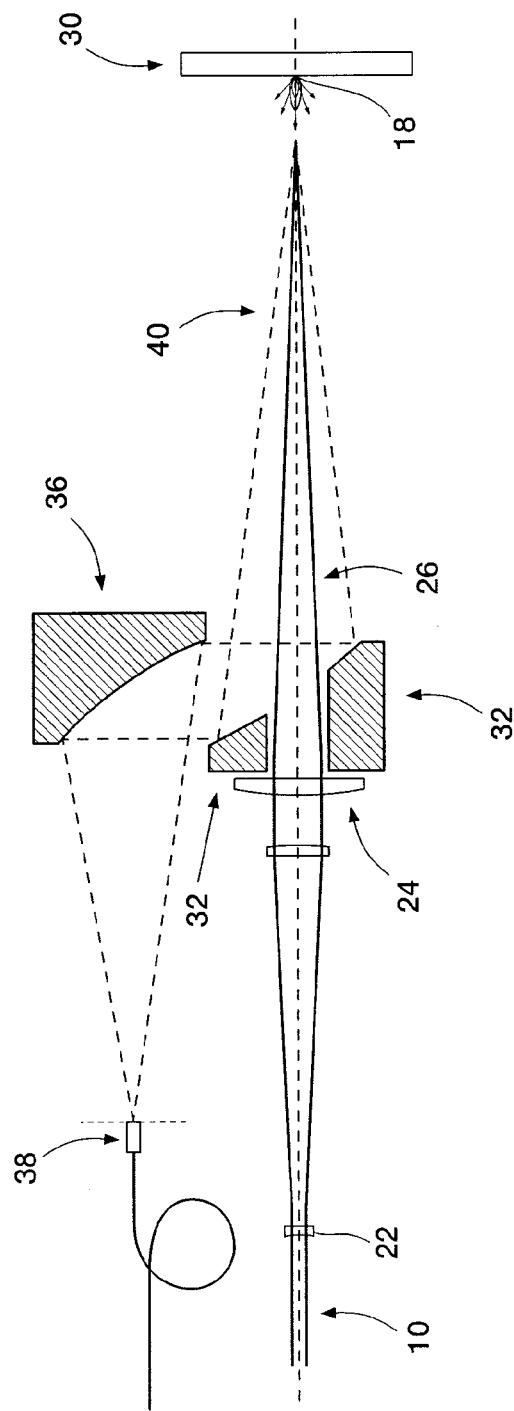
FIG. 11 is a diagram illustrating one embodiment of the present invention wherein achromatic reflective optics are used to detect light emitted from the plasma plume.

For the purpose of performing the rough adjustment step, the photodiode 7 in FIG. 4 can be attached to the inner structure of the light confinement chamber 8, near the output aperture, with the sensitive surface of the photodiodes directed towards the location of impact of the laser beam on the target surface, namely where the plasma plume 11 is to be generated. Alternatively, a single core optical fiber can be positioned close to the image of the plasma in focal plane 24 as illustrated in FIG. 11 and discussed in further detail below, for the purpose of collecting and transporting the light emitted from the plasma plume onto the photodetector surface, which may then be remotely positioned elsewhere in the device.

As discussed in relation to FIG. 13 below, an algorithm is described, which performs a method to accurately bring the focusing plane 16 in coincidence with the target surface 18.

As ablation continues, sample material from the target surface 18 of sample 30 is removed and the actual target surface moves distally away from the laser source to create a second target surface 19, as seen in FIG. 5C. These conditions may not be suitable for continued ablation of the sample as the focusing plane 16 of resultant laser beam 26 is no longer coincident with the second target plane 19 of the sample 30. Accordingly, the focal length of incident laser beam can be increased such that the focusing plane 16 of the resultant laser beam 26 is coincident with second target plane 19 in order to generate ablation and plasma emission at the target surface 19, as seen in FIG. 5D.

It is also desirable to take a number of samples at various positions on the target surface of the sample, as will be readily understood by the skilled person. For example, multiple sample analyses can provide further insight into the homogeneity of the sample. Turning to FIG. 6, in at least one embodiment it is contemplated that the present method and apparatus can be configured such that the resultant laser beam can be moved radially from a first target position to a second target position. This requires that the resultant laser beam can be manipulated such that its beam diameter can be minimized (to maximize laser fluency), its focal length can be manipulated (to ensure that the focusing plane is substantially coincident with the target plane), and moved radially (or in the context of a rectangular coordinate system, laterally, horizontally or vertically) from a first target position to at least a second target position.

With reference to FIGS. 6, 7, 8, 9 and 10, it is contemplated that this can be achieved in a number of ways in accordance with embodiments of the present invention. An incident laser beam 10 can optionally be directed through pre-optical lenses 22 and directed towards optical means 24 which reduce the diameter and focal length of the beam to create a reduced diameter resultant laser beam 26 such that the focusing plane 16 of the laser beam is substantially coincident with the target surface 18 of a sample 30 in order to substantially maximize laser fluency at the target surface 18. However, in this embodiment, optical means 24 further have the ability to radially translate the resultant laser beam 26 from a first target position to a second target position as seen in FIG. 7.

In this embodiment it is contemplated that optical means 24 can take a wide variety of forms as will be readily understood by the skilled person, including, but not limited to, triple-axis electronically tunable lenses, Risley prisms pairs, translatable focusing lenses and translatable beam reducing lenses, among other suitable arrangements and combinations thereof for reducing laser beam diameter and shortening laser beam focal length.

Figure 8:
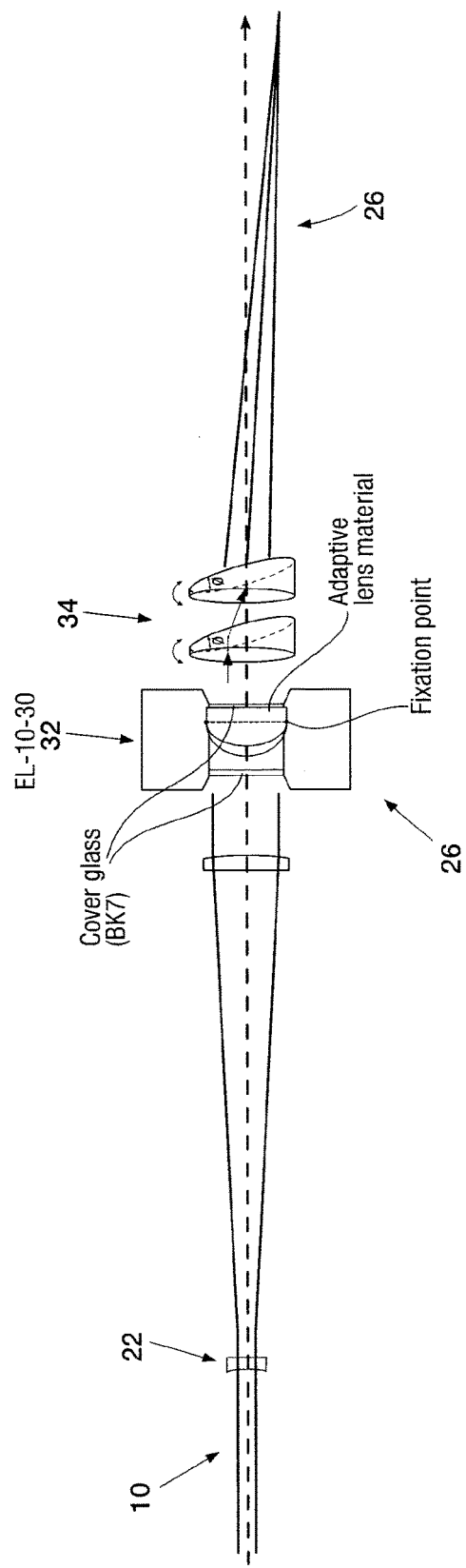
FIG. 8 is a diagram of the embodiment illustrated in FIGS. 6 and 7 wherein the optical means for manipulating the laser beam is a Risley prisms pair in connection with an electronically tunable focusing lens.
Figure 9:
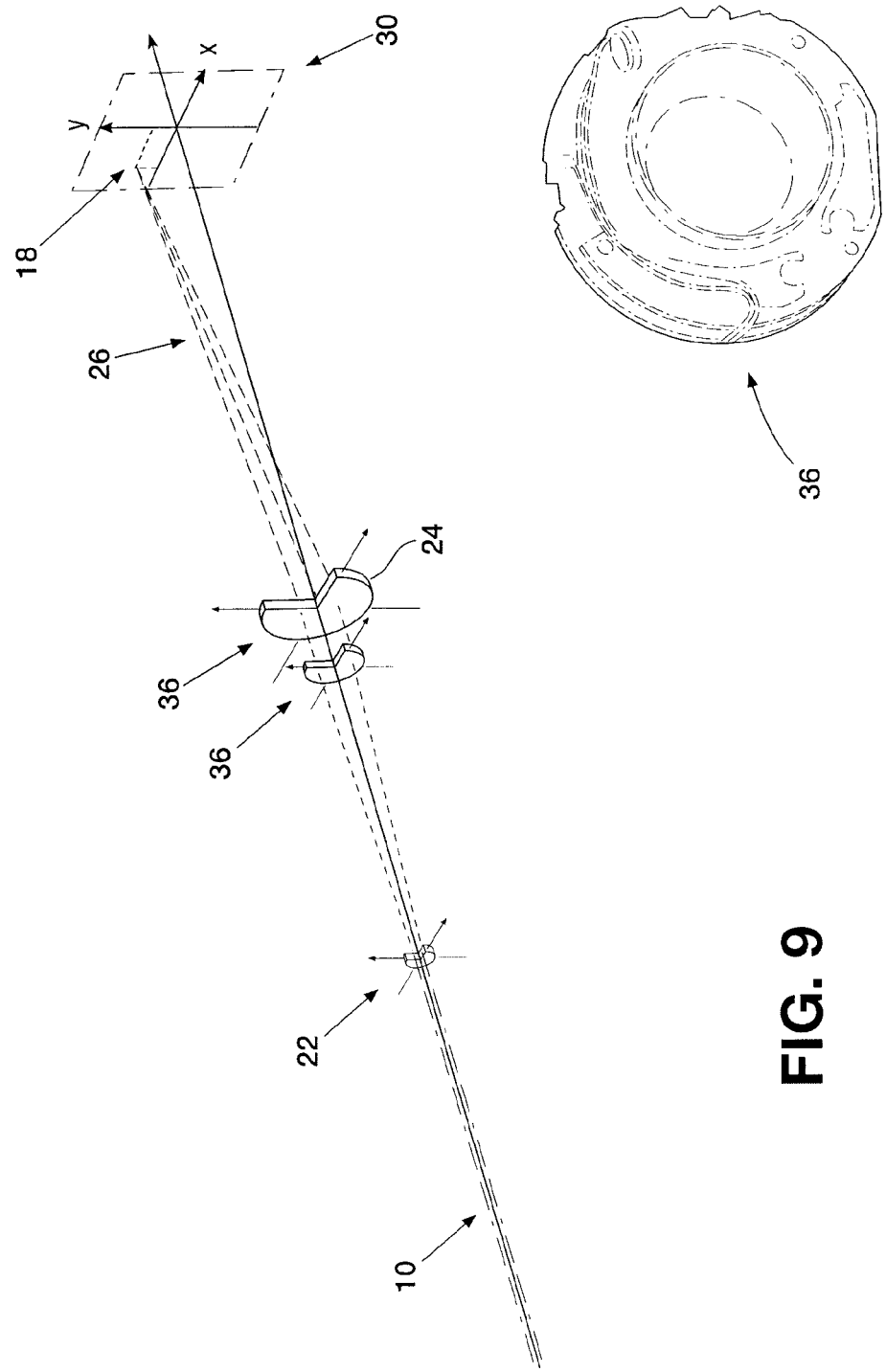
FIG. 9 is a diagram of the embodiment illustrated in FIGS. 6 and 7 wherein the optical means for manipulating the laser beam is an axially translating focusing lens.
Figure 10:
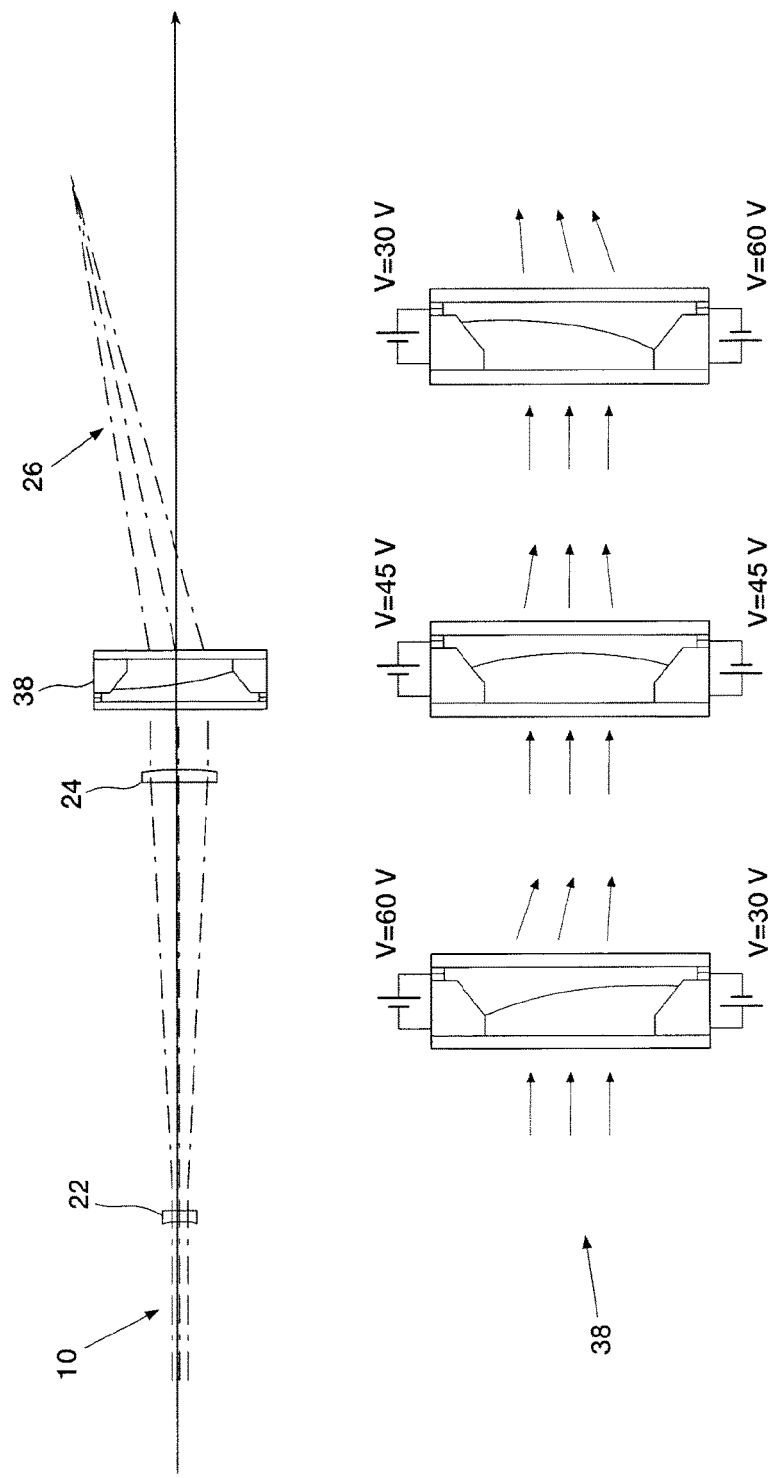
FIG. 10 is a diagram of the embodiment illustrated in FIGS. 6 and 7 wherein the optical means for manipulating the laser beam is a triple-axis electronically tunable focusing lens.

In this way, optical means 24 can be used to radially (or laterally, horizontally or vertically depending on the coordinate system used) move the resultant laser beam from a first position to a second position in order to take multiple samples of the same surface. As seen in FIG. 8, this can be accomplished with a single access electronically tunable lens 32 and a Risley prisms pair 34, translatable focusing and beam reducing lenses 36 (as seen in FIG. 9) or a triple axis electronically tunable lens 38 (as seen in FIG. 10).

It is contemplated that LIBS samples can be taken randomly across the surface of sample 30, or alternatively multiple LIBS samples can be taken from positions selected based on a predetermined pattern or random beam sweep pattern, among other arrangements that will be readily appreciated by the skilled person.

According to embodiments, in order to provide an accurate and sensitive analysis, it is desirable to use an optical configuration that allows collection of light emitted by a plasma plume with the same efficiency over the whole range of spectral interest. This can be achieved by positioning a variety of mirrors opposite and adjacent from the sample such that light emitted from the excited sample at a larger number of angles can be collected and reflected to the detector.

As will be readily understood by a skilled person, a detector has a relatively narrow field of detection that can only detect light reflected within that field of detection. Therefore, it is desirable to collect light across as wide of a field of detection as possible and reflect it back into the narrower field of detection of the detector, in a manner analogous to that of a satellite dish or parabolic antennae.

With reference to FIG. 11, in at least one embodiment of the present invention this collection can be accomplished by introducing achromatic reflective optics to the arrangements discussed above. An incident laser beam 10 is generated by a laser source and directed through optional pre-optical lenses 22. Incident laser beam 10 reaches optical means 24 where the focal length is altered and the laser beam diameter is reduced to bring the focusing plane of the resultant laser beam 26 substantially coincident with the target plane of the sample 30 in order to initiate ablation and plasma emission from the target plane of sample 30.

As ablation and plasma emission progresses, light 40 is emitted across a particular field of emission. In this embodiment, achromatic reflective optics are provided in the form of a concavely parabolic mirror 32 which is oriented adjacent from and opposed to sample 30. A cylindrical center portion of mirror 32 is hollowed out from its bulk mass to allow thru-passing of the laser beam from the optical focusing component towards the target plane. Parabolic mirror 32 reflectively communicates with an additional off-axis concavely parabolic mirror 36 that further communicates with detector 38 of a spectrometer (not shown). In this way, light reflected across a relatively wide range of detection can be reflected into the relatively narrow field of detection of detector 38 to substantially maximize the collection of light 40 from the sample over a wide range of spectral interest.

However, it is contemplated that a wide variety of achromatic reflective optics arrangements can be used in connection with the present invention in order to substantially maximize the collection of light from the sample over a wide range of spectral interest. For example, it is contemplated that the present invention could utilize a single parabolic mirror communicating with an additional off-axis concavely parabolic mirror, or alternatively the additional off-axis concavely parabolic mirror may further communicate with yet another off-axis concavely parabolic mirror, among other suitable arrangements that will readily appreciated by the skilled person.

Figure 12:
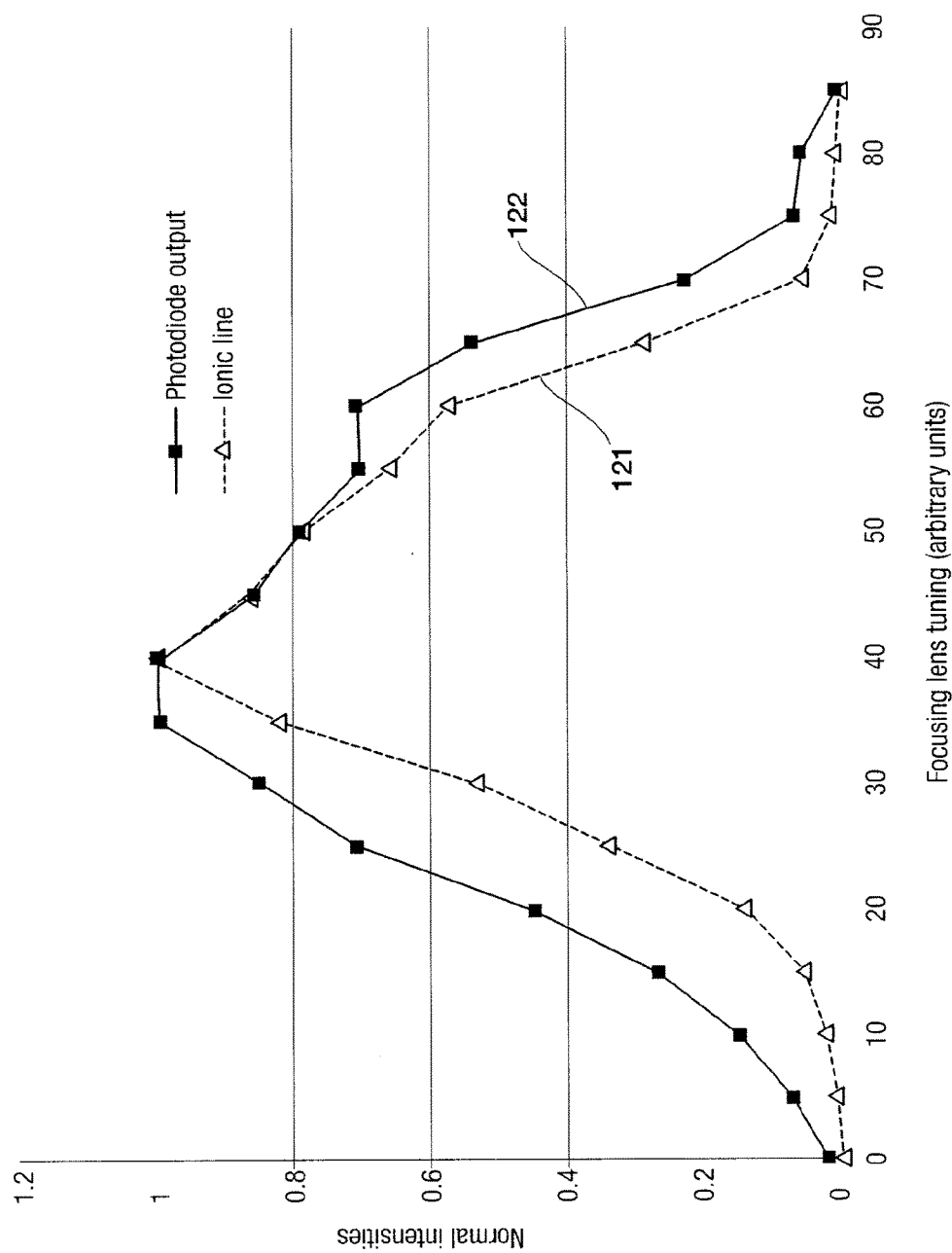
FIG. 12 is a graph showing the evolution of (i) the intensity of an ionic line and (ii) the signal provided by a photodetector which measures the light emitted from the plasma, as a function of the tuning parameter of an electronically tunable focusing lens.

Turning to FIG. 12, a chart is illustrated wherein normalized intensities are plotted against an arbitrary focusing lens tuning unit. As can be seen, the focusing lens can be incrementally adjusted along a unitless, arbitrary scale of 1 to 100 and when the normalized intensity of the ionic line 121 is coincident with the normalized intensity of the photodiode output 122, a maximum coincident normalized intensity is plotted, thereby giving an idealized indication of how the focusing lens should be tuned. As seen in FIG. 12, when a normalized intensity of 1.0 is achieved for both the ionic line and the photodiode output, it is indicated that the focusing lens is set at 40 (which in the present teaching, is an arbitrarily chosen and unitless value). Given that the width of the ionic line intensity profile is narrower than the photodiode output signal profile, the final lens tuning step relying on the ionic intensity profile as the feedback parameter will provide a higher level of sensitivity and precision than using the photodiode signal profile alone, as will be readily understood by the skilled person.

Figure 13:
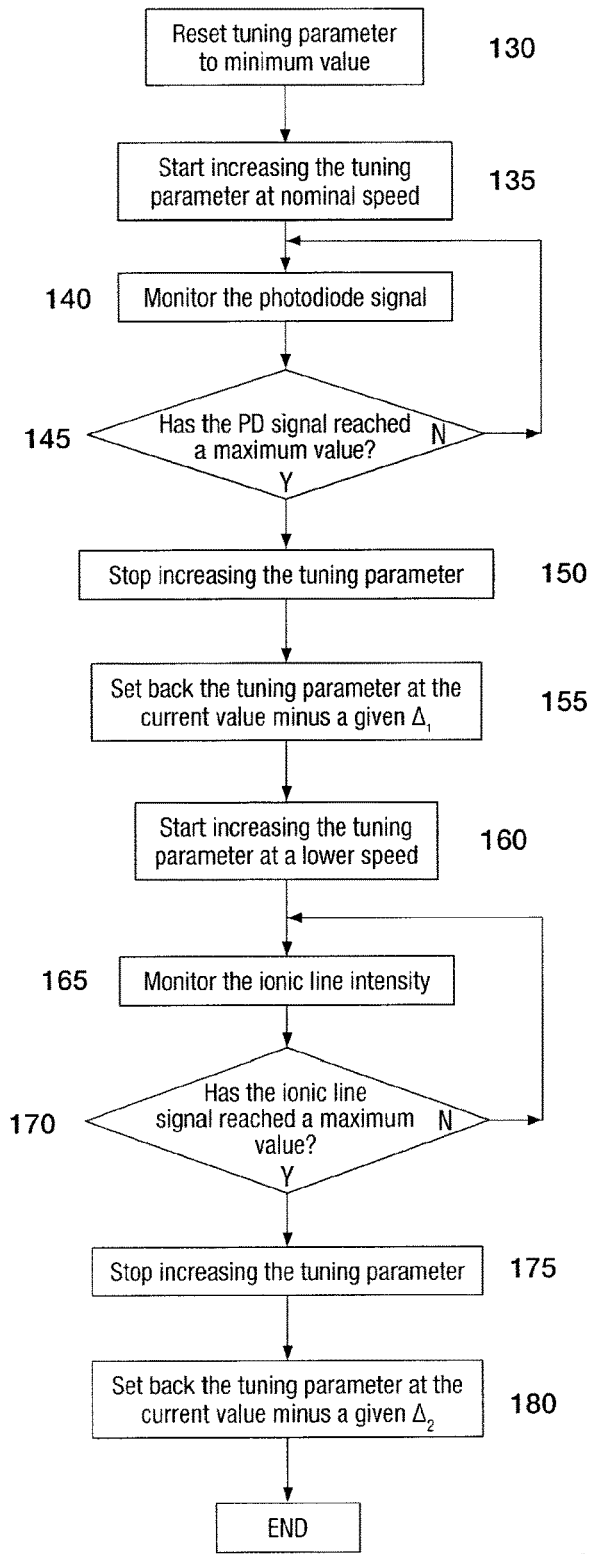
FIG. 13 is a flow chart describing a procedure for the accurate focusing of the laser beam spot onto the target surface.

Turning to FIG. 13, at least one embodiment of a method for the accurate focusing of the laser beam spot onto the target surface is illustrated. First, at the outset of the ablation procedure for a particular sample surface, the tuning parameter of the focusing lens is set to a minimum value 130. Next, this tuning parameter is slowly increased at a nominal speed 135, while the resultant photodiode signal is continually monitored 140 to determine when the photodiode signal reaches a maximum value 145.

Once the photodiode signal has reached a maximum value, the tuning parameter is not increased any further 150. The tuning parameter may then be reset by a small amount 155 and slowly increased at a lower rate 160 than previously. Simultaneously, the ionic line intensity can be monitored 165 to determine when the ionic line intensity has reached a maximum value 170.

At this point the tuning parameter is no longer increased 175, and may then be reset by a small amount 180 in anticipation of the subsequent ablation of the sample.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

We claim:

1. A method of laser induced breakdown spectroscopy comprising:
    directing a laser beam to a target plane on a sample, the target plane located on a proximal surface of the sample;
    manipulating the laser beam to substantially maximize threshold fluency at the target plane;
    generating ablation and plasma emission from the sample at the target plane; wherein manipulating the laser beam to substantially maximize threshold fluency at the target plain is performed with an optical instrument;
    wherein the optical instrument is an electronically tunable lens and further comprises a photodiode generating a photodiode output and wherein manipulating the laser beam to substantially maximize threshold fluency at the target plane is achieved by adjusting the electronically tunable lens such that a normalized intensity of the photodiode output is coincident with an observed normalized intensity of ionic lines detected from the sample during ablation and plasma emission of the sample.

2. The method of claim 1 wherein manipulating the laser beam to substantially maximize threshold fluency at the target plane further comprises focusing the laser beam on the target plane to create a resultant laser beam such that a focusing plane of the resultant laser beam is substantially coincident with the target plane.

3. The method of claim 1 wherein manipulating the laser beam to substantially maximize threshold fluency at the target plane further comprises reducing a diameter of the laser beam.

4. The method of claim 1 wherein the sample degrades at the target plane due to ablation of the sample thereby creating a second target plane on the sample distally removed from the target plane, the method further comprising:
   manipulating the laser beam to substantially maximize threshold fluency at the second target plane resulting in a second resultant laser beam such that the focusing plane of the second resultant laser beam is substantially coincident with the second target plane; and
   generating ablation and plasma emission from the sample at the second target plane.

5. The method of claim 4 wherein manipulating the laser beam to substantially maximize threshold fluency at the second target plane further comprises focusing the laser beam on the second target plane.

6. The method of claim 4 wherein manipulating the laser beam to substantially maximize threshold fluency at the second target plane further comprises moving the laser beam to a radially disposed second position, the second position selected from a random beam sweep pattern.

7. The method of claim 4 wherein manipulating the laser beam to substantially maximize threshold fluency at the second target plane further comprises reducing a diameter of the laser beam.

8. The method of claim 4 wherein manipulating the laser beam to maximize threshold fluency at the second target plane is performed with an optical instrument selected from the group consisting of: a single-axis electronically tunable lens, a focusing lens, a beam reducing lens and combinations thereof.

9. The method of claim 1 further comprising the steps of:
   detecting a plasma plume emanating from the sample, and
   spectroscopically analyzing the plasma plume to determine chemical composition of the sample.

10. The method of claim 9 wherein the plasma plume is detected using achromatic reflective optics.

11. The method of claim 10 wherein the achromatic reflective optics are a plurality of concavely parabolic mirrors, each of the plurality of concavely parabolic mirrors having a reflective surface facing the sample, each of the plurality of concavely parabolic mirrors radially removed from a central axis that is coincident with the laser beam, each of the plurality of concavely parabolic mirrors visually communicating with an emission spectrometer.

12. The method of claim 11 further comprising an auxiliary parabolic mirror, the auxiliary concavely parabolic mirror radially removed from the central axis, the auxiliary parabolic mirror visually communicating with each of the plurality of mirrors and the emission spectrometer.

13. A method of laser induced breakdown spectroscopy comprising:
   directing a laser beam to a target plane on a sample, the target plane located on a proximal surface of the sample;
   manipulating the laser beam to substantially maximize threshold fluency at the target plane;
   generating ablation and plasma emission from the sample at the target plane;
   redirecting the laser beam to a first radially removed target plane, the first radially removed target plane radially displaced from the target plane;
   manipulating the laser beam to substantially maximize threshold fluency at the first radially removed target plane thereby creating a resultant redirected laser beam such that the focusing plane of the resultant redirected laser beam is substantially coincident with the first radially removed target plane; and
   generating ablation and plasma emission from the sample at the first radially removed target plane target plane.

14. The method of claim 13 wherein manipulating the laser beam to substantially maximize threshold fluency at the first radially removed target plane further comprises focusing the laser beam on the target plane.

15. The method of claim 13 wherein manipulating the laser beam to substantially maximize threshold fluency at the first radially removed target plane further comprises reducing a diameter of the laser beam.

16. The method of claim 13 wherein the first radially removed target plane is selected from a random beam sweep pattern.

17. The method of claim 13 wherein manipulating the laser beam to substantially maximize threshold fluency at the first radially removed target plane is performed with an optical instrument selected from the group consisting of: a Risley prisms pair, a three-axis electronically tunable lens, a radially translating focusing lens and combinations thereof.

18. An apparatus for laser induced breakdown spectroscopy of a sample comprising:
   a laser source generating a laser beam, the laser beam directed to the sample;
   optical means for manipulating the laser beam to substantially maximize laser fluency at a target surface of the sample, the laser beam generating ablation and plasma emission from the sample at the target surface;
   an emission spectrometer having a detector for detecting a plasma plume from the plasma emission; and
   wherein the optical means are selected from the group consisting of a three-axis electronically tunable lens and a single-axis electronically tunable lens and wherein the optical means further comprises a photodiode adapted to generate a photodiode output.

19. The apparatus for laser induced breakdown spectroscopy of claim 18 wherein the optical means is further configured to focus the laser beam on the target surface to create a resultant laser beam such that a focusing plane of the laser beam is substantially coincident with the target surface of the sample.

20. The apparatus for laser induced breakdown spectroscopy of claim 18 wherein the optical means is further configured to reduce a diameter of the laser beam.

21. The apparatus of claim 18 wherein the plasma emission is detected using achromatic reflective optics.

22. The apparatus of claim 21 wherein the achromatic reflective optics are a plurality of concavely parabolic mirrors, each of the plurality of concavely parabolic mirrors having a reflective surface facing the sample, each of the plurality of concavely parabolic mirrors radially removed from a central axis that is coincident with the laser beam, each of the plurality of concavely parabolic mirrors visually communicating with the detector of the emission spectrometer.

23. The apparatus of claim 22 further comprising an auxiliary parabolic mirror, the auxiliary concavely parabolic mirror radially removed from the central axis, the auxiliary concavely parabolic mirror visually communicating with each of the plurality of concavely parabolic mirrors and the detector of the emission spectrometer.

\* \* \* \* \*